(12) United States Patent
Naubereit

(10) Patent No.: US 12,245,973 B2
(45) Date of Patent: Mar. 11, 2025

(54) METHOD FOR CONTROLLING AN OPTHALMOLOGICAL LASER AND TREATMENT APPARATUS

(71) Applicant: SCHWIND EYE-TECH-SOLUTIONS GMBH, Kleinostheim (DE)

(72) Inventor: Pascal Naubereit, Aschaffenburg (DE)

(73) Assignee: SCHWIND EYE-TECH-SOLUTIONS GMBH, Kleinostheim (DE)

( * ) Notice: Subject to any disclaimer, the term of this patent is extended or adjusted under 35 U.S.C. 154(b) by 0 days.

(21) Appl. No.: 17/705,966

(22) Filed: Mar. 28, 2022

(65) Prior Publication Data

US 2022/0347016 A1 Nov. 3, 2022

(30) Foreign Application Priority Data

Apr. 30, 2021 (DE) .................. 10 2021 111 266.4

(51) Int. Cl.
*A61F 9/008* (2006.01)
*A61B 18/00* (2006.01)
*A61B 18/20* (2006.01)
*A61D 1/00* (2006.01)

(52) U.S. Cl.
CPC ........ *A61F 9/00814* (2013.01); *A61F 9/0084* (2013.01); *A61B 2018/00732* (2013.01); *A61B 2018/00761* (2013.01); *A61B 2018/20355* (2017.05); *A61D 1/00* (2013.01); *A61F 2009/00842* (2013.01); *A61F 2009/0087* (2013.01); *A61F 2009/00872* (2013.01); *A61F 2009/00897* (2013.01)

(58) Field of Classification Search
CPC ................ A61F 9/00814; A61F 9/0084; A61F 2009/00842; A61F 2009/0087; A61F 2009/00872; A61F 2009/00897; A61B 2018/20355; A61B 2018/00732; A61B 2018/00761

See application file for complete search history.

(56) References Cited

U.S. PATENT DOCUMENTS

| 4,843,468 A * | 6/1989 | Drewery .................. H04N 3/30 345/428 |
| 2005/0107775 A1* | 5/2005 | Huang .................... A61F 9/008 606/5 |
| 2019/0105200 A1* | 4/2019 | Hipsley .................. A61F 9/008 |

FOREIGN PATENT DOCUMENTS

JP 201655526 A 4/2016

OTHER PUBLICATIONS

Office Action issued Jan. 21, 2022 in DE Appl. No. 10 2021 111 266.4.

* cited by examiner

*Primary Examiner* — Gary Jackson
*Assistant Examiner* — Skylar Lindsey Christianson
(74) *Attorney, Agent, or Firm* — MEDLER FERRO WOODHOUSE & MILLS PLLC

(57) ABSTRACT

A method is disclosed for controlling an ophthalmological laser of a treatment apparatus for the treatment of a human or animal eye. The method includes controlling the laser by a control device of the treatment apparatus such that the laser emits pulsed laser pulses in a shot sequence in a preset pattern into the eye. The individual laser pulses interact with a tissue of the eye for the treatment of the eye, wherein a space-filling curve is the preset pattern for treating the tissue.

15 Claims, 2 Drawing Sheets

METHOD FOR CONTROLLING AN OPTHALMOLOGICAL LASER AND TREATMENT APPARATUS

FIELD

The invention relates to a method for controlling an ophthalmological laser of a treatment apparatus for the treatment of a human or animal eye. Further, the invention relates to a control device, to a treatment apparatus with a control device, to a computer program as well as to a computer-readable medium.

BACKGROUND

From the prior art, different laser methods are known, which emit pulsed laser pulses in a preset pattern into the eye, in particular into a cornea or a lens of the eye, by means of corresponding treatment apparatuses, for example to treat a visual disorder, in particular hyperopia or myopia, or opacities.

Herein, straight or singly curved as well as concentric paths or combinations of them are usually used as the patterns in the two- or three-dimensional space. In refractive applications within the cornea or the lens, both in a laser induced refractive index change (LIRIC) and in photoablative or photodisruptive incisions, undesired diffraction errors can occur by a repetitive arrangement of such patterns, such as for example undesired multifocal effects and chromatic aberrations (e.g. rainbow glare). Further types of imaging errors can also arise.

SUMMARY

It is the object of the present invention to provide a method, a treatment apparatus, a computer program as well as a computer-readable medium, by means of which these effects can be reduced.

This object is solved by a method, a treatment apparatus, a control device, a computer program as well as a computer-readable medium according to the independent claims. Advantageous configurations with convenient developments of the invention are specified in the respective dependent claims, wherein advantageous configurations of the method are to be regarded as advantageous configurations of the treatment apparatus, of the control device, of the computer program and of the computer-readable medium and vice versa.

A first aspect of the invention relates to a method for controlling an ophthalmological laser of a treatment apparatus for the treatment of a human or animal eye. Control of the laser by means of a control device of the treatment apparatus such that it emits pulsed laser pulses in a shot sequence in a preset pattern into the eye is effected, wherein the individual laser pulses interact with a tissue of the eye for the treatment of the eye, wherein a space-filling curve is preset for the pattern for treating the tissue.

In other words, the ophthalmological laser is controlled such that a pattern of a space-filling curve is irradiated into a tissue of the eye. For example, it can be provided to separate a lenticule from a cornea, which comprises anterior and posterior interfaces, and a cavitation bubble pattern can be generated in the cornea for separating the respective interface from the cornea, which comprises a space-filling curve as the preset pattern. A space-filling curve is a mathematical curve in the field of analysis, which completely passes through a two-dimensional surface or a three-dimensional space, thus is surjective. At the same time, such a curve is not bijective and continuous at the same time. This means that the space-filling curve describes a contiguous curve, which passes through the entire tissue to be treated. In addition, the space-filling curve can comprise diverse abrupt or sharp direction changes to cover the entire tissue to be treated. Known structures, which can be generated by space-filling curves, are in particular fractal curves (fractals). Hereby, the advantage arises that the generation of recurring and/or symmetrical structures can be avoided, which can in particular result in undesired multifocal effects.

The invention also includes configurations, by which additional advantages arise.

In an advantageous form of configuration, it is provided that the space-filling curve is preset in self-avoiding manner. By self-avoiding, it is meant that the curve does not intersect itself. This has the advantage that a double irradiation of the curve at possible points of intersection does not occur and therefore an expensive beam control for achieving a constant laser pulse distance can be avoided.

In a particularly advantageous form of configuration, it is provided that a fractal is preset as the space-filling curve. A fractal is a space-filling curve, which is self-avoiding and has a self-similar structure. This means that partial areas of a fractal are a copy of the whole. Fractals are known from the mathematics and in particular were characterized by the mathematician Benoit Mandelbrot. In particular, fractals differ in essential aspects from smooth figures, which were used as curves for the treatment of the eye up to now. A regularly arranged diffraction structure, Fresnel lenses or the like can be interrupted by fractals in that virtually irregular structures are scanned by the fractal curves. By this form of configuration, a particularly preferred pattern can be preset for the shot sequence of the laser pulses.

Preferably, it is provided that the fractal is preset as a Gosper curve, Hilbert curve or Peano curve. In particular the previously mentioned fractals allow a particularly advantageous adaptation of the space-filling curve to a geometry of the eye, in particular of the cornea or the lens of the eye.

In a further form of configuration, it is provided that the laser is controlled such that the laser pulses generate the space-filling curve in continuous manner. This means that the space-filling curve is generated in uninterrupted manner or without breaking and thus a gapless contiguous space-filling curve is generated. Thus, it can be ensured that gaps or structures are not generated, which generate negative optical effects.

In a further advantageous form of configuration, it is provided that the laser is controlled such that the laser pulses generate the space-filling curve line by line or in concentric or spiral manner. In other words, scanning the laser over the eye can be controlled according to a usual pattern, wherein irradiation of the laser pulses can be effected only in those positions, in which a point of the space-filling curve is to be generated. This means that a tissue of the eye can for example be scanned raster by raster, in particular in line-shaped, concentric or spiral manner, and the irradiation of the respective laser pulses can be effected only in the positions of the space-filling curve. Herein, the advantage arises that a deflection of the laser beam can be simplified. Thereby, the pattern can be faster generated than if the laser is controlled along the space-filling curve.

Preferably, it is provided that the laser pulses are emitted into a cornea and/or a lens of the eye. In particular, preset patterns can be used to generate one or more incisions in a cornea, for example a so-called flap or a lenticule, and/or the preset pattern can be applied in methods for laser induced refractive index changes in the cornea or the lens of the eye.

A second aspect of the present invention relates to a control device, which is configured to perform one of the above described methods. The above cited advantages arise. For example, the control device can be configured as a control chip, control unit or application program ("app"). Preferably, the control device can comprise a processor device and/or a data storage. An appliance or an appliance component for electronic data processing is understood by a processor device. The processor device can for example comprise at least one microcontroller and/or at least one microprocessor. Preferably, a program code for performing the method according to the invention can be stored on the optional data storage. The program code can then be adapted, upon execution by the processor device, to cause the control device to perform one of the above described embodiments of one or both methods according to the invention.

A third aspect of the present invention relates to a treatment apparatus with at least one ophthalmological laser for the treatment of a tissue predefined by the control data, in particular of a corneal volume with predefined interfaces of a human or animal eye by means of photodisruption and/or photoablation and/or a laser induced refractive index change, and at least one control device for the laser or lasers, which is formed to execute the steps of the method according to the first aspect of the invention. The treatment apparatus according to the invention allows that the disadvantages occurring in the use of usual treatment apparatuses are reliably reduced or even avoided.

In a further advantageous configuration of the treatment apparatus according to the invention, the laser can be suitable to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kilohertz (kHz), preferably between 100 kHz and 100 megahertz (MHz). Such a femtosecond laser is particularly well suitable for removing tissue within the cornea. The use of photodisruptive and/or photoablative lasers in the method according to the invention additionally has the advantage that the irradiation of the cornea does not have to be effected in a wavelength range below 300 nm. This range is subsumed by the term "deep ultraviolet" in the laser technology. Thereby, it is advantageously avoided that an unintended damage to the cornea is effected by these very short-wavelength and high-energy beams. Photodisruptive lasers of the type used here usually input pulsed laser radiation with a pulse duration between 1 fs and 1 ns into the corneal tissue. Thereby, the power density of the respective laser pulse required for the optical breakthrough can be spatially narrowly limited such that a high incision accuracy is allowed in the generation of the interfaces. In particular, the range between 700 nm and 780 nm can also be selected as the wavelength range.

In a further advantageous configuration of the treatment apparatus according to the invention, the laser can be suitable to emit laser pulses in a wavelength range between 150 nm and 250 nm, preferably between 175 nm and 215 nm, at a respective pulse duration between 1 fs and 100 ns, preferably between 10 ps and 10 ns, and a repetition frequency of greater than 100 Hertz (Hz), preferably between 400 Hz and 10 kilohertz (MHz). Such an ablation laser, which can in particular be formed as an excimer laser, is particularly well suitable for ablating tissue of the cornea. The use of lasers in a wavelength range below 300 nm, which is also referred to as "deep ultraviolet", can particularly efficiently ablate the tissue from the cornea by these very short-wavelength and high-energy beams. Photoablative lasers of the type used here usually input pulsed laser radiation with a pulse duration between 1 fs and 100 ns into the corneal tissue. In particular, the range between 175 nm and 215 nm can also be selected as the wavelength range.

In further advantageous configurations of the treatment apparatus according to the invention, the control device can comprise at least one storage device for at least temporary storage of at least one control dataset, wherein the control dataset or datasets include(s) control data for positioning and/or for focusing individual laser pulses in the eye, in particular the cornea; and can comprise at least one beam device for beam guidance and/or beam shaping and/or beam deflection and/or beam focusing of a laser beam of the laser. Therein, the mentioned control dataset includes the control data determined in the method for removing the tissue.

Further features and the advantages thereof can be taken from the descriptions of the first inventive aspect, wherein advantageous configurations of each inventive aspect are to be regarded as advantageous configurations of the respectively other inventive aspect.

A fourth aspect of the invention relates to a computer program including commands, which cause the treatment apparatus according to the third inventive aspect to execute the method steps according to the first inventive aspect and/or the method steps according to the second inventive aspect.

A fifth aspect of the invention relates to a computer-readable medium, on which the computer program according to the fourth inventive aspect is stored. Further features and the advantages thereof can be taken from the descriptions of the first to fourth inventive aspects, wherein advantageous configurations of each inventive aspect are to be regarded as advantageous configurations of the respectively other inventive aspect.

BRIEF DESCRIPTION OF DRAWINGS

Further features of the invention are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

In the figures, identical or functionally identical elements are provided with the same reference characters.

DETAILED DESCRIPTION

Figure 1:
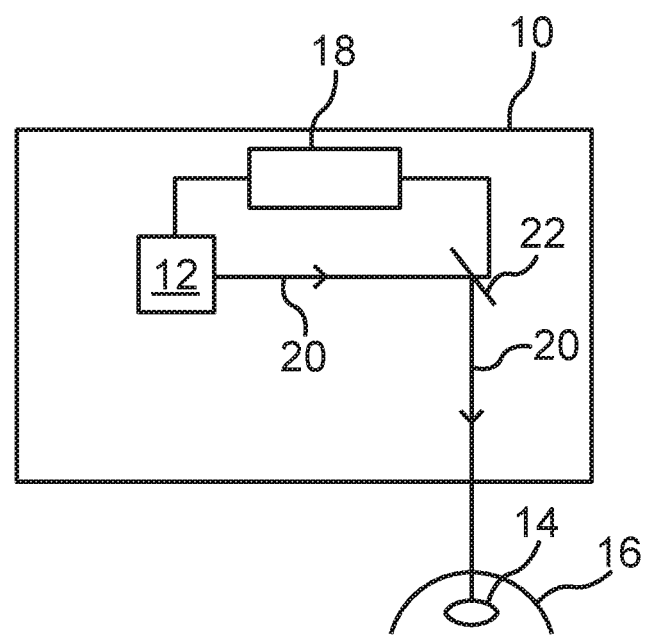
FIG. 1 depicts a schematically illustrated treatment apparatus according to an exemplary embodiment.

FIG. 1 shows a schematic representation of a treatment apparatus 10 with an ophthalmological laser 12 for the treatment of an eye 16, wherein a tissue 14, in particular a volume body 14, is removed from a human or animal cornea by means of photodisruption and/or photoablation in this embodiment. For example, the volume body 14 can be separated from a cornea of an eye 16 for correcting a visual disorder by the eye surgical laser 12. A predefined pattern for removing the volume body 14 can be provided by a control device 18, in particular in the form of control data, such that the laser 12 emits pulsed laser pulses into the cornea of the eye 16 in a pattern predefined by the control data, to form an anterior interface and a posterior interface, which together result in the volume body 14. Alternatively, the control device 18 can be a control device 18 external with respect to the treatment apparatus 10.

Furthermore, FIG. 1 shows that the laser beam 20 generated by the laser 12 can be deflected towards the cornea 16 by means of a beam deflection device 22, such as for example a rotation scanner, to separate the volume body 14. The beam deflection device 22 can also be controlled by the control device 18 to remove the volume body 14.

The illustrated laser 12 can preferably be a photodisruptive and/or photoablative laser, which is formed to emit laser pulses in a wavelength range between 300 nanometers and 1400 nanometers, preferably between 700 nanometers and 1200 nanometers, at a respective pulse duration between 1 femtosecond and 1 nanosecond, preferably between 10 femtoseconds and 10 picoseconds, and a repetition frequency of greater than 10 kilohertz, preferably between 100 kilohertz and 100 megahertz. Optionally, the control device 18 additionally comprises a storage device (not illustrated) for at least temporary storage of at least one control dataset, wherein the control dataset or datasets include(s) control data for positioning and/or for focusing individual laser pulses in the cornea.

One problem in the removal of the volume body 16 with conventional approaches is in that undesired diffraction errors can occur. In particular if concentric paths are used for the preset pattern, it can result in multifocal effects, which can impair a vision. Therefore, it is provided that a space-filling, preferably self-avoiding, simple and self-similar curve is used for the control of the laser 12. In particular fractals satisfy this characteristic and are particularly suitable to avoid a development of microlenses during the treatment.

Figure 2:
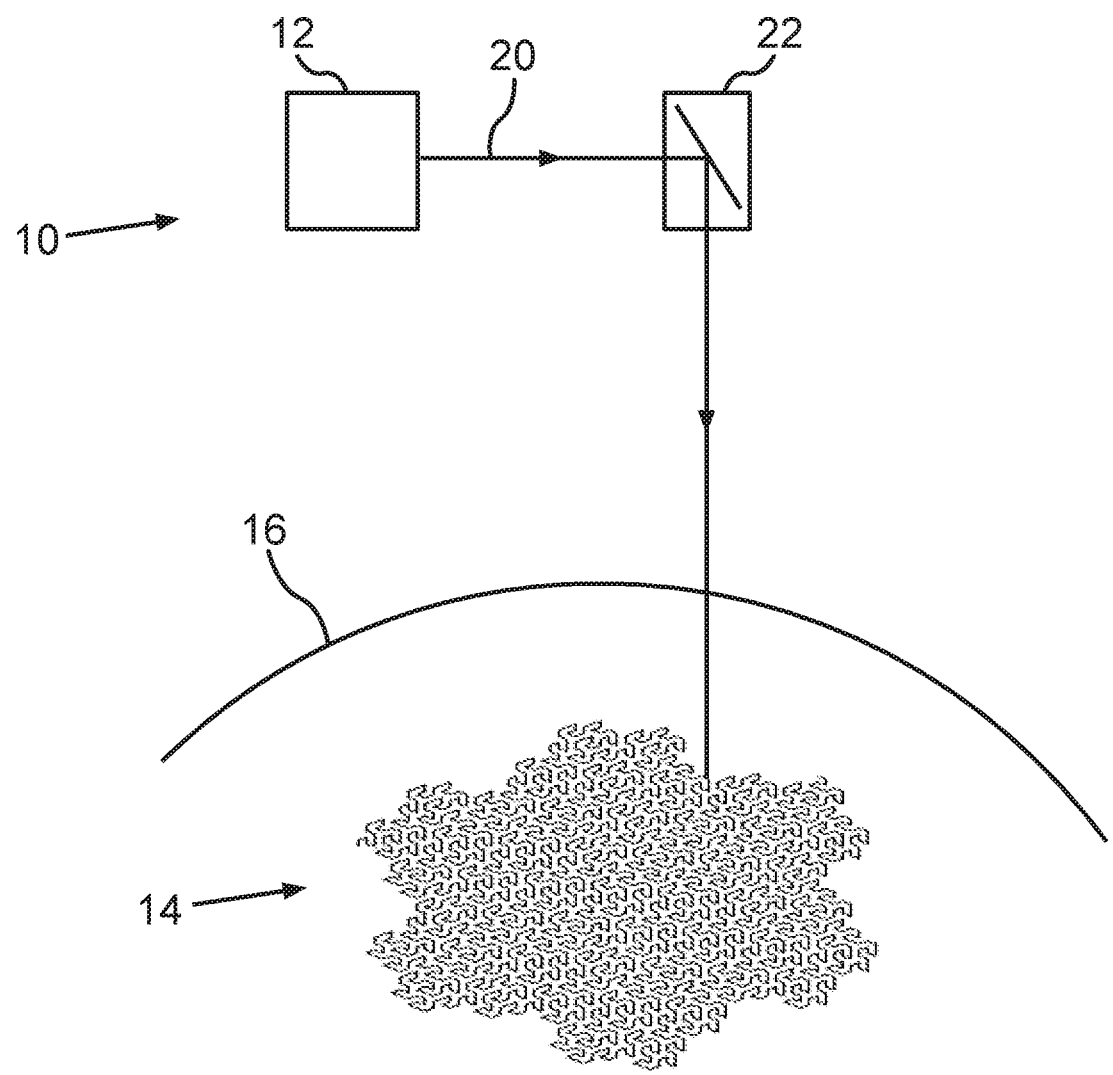
FIG. 2 depicts a section of a schematically illustrated treatment apparatus according to an exemplary embodiment.

In FIG. 2, it is schematically illustrated how the treatment apparatus 10 can remove the volume body 14, in particular a respective interface of the volume body 14, by means of a preset fractal pattern. Herein, the laser 12 irradiates pulsed laser pulses 20, which are irradiated into the eye 16 via the beam deflection device 22. Control data can be stored in the control device 18, which control the beam deflection device 22 such that the laser beam generates the fractal pattern. In this example, a Gosper curve can be generated in a posterior and in an anterior surface, whereby the lenticule 14 can be subsequently removed.

For generating the fractal, the fractal curve can be generated by the beam deflection device 22 in continuous manner, that means that the laser beam 20 can be guided along the path of the fractal curve. Alternatively, the control device can also scan the interface to be removed line by line, in spiral or concentric manner, wherein the laser 12 can preferably be configured such that the laser pulses of the laser beam 20 are only irradiated if the current position matches the curve of the fractal. This has the advantage that the space-filling curve can be faster generated since the beam deflection device 22 can be simpler controlled.

Here, the control of the laser 12 was described based on the example of an incision in the cornea for removing a volume body 14. The use of space-filling curves, in particular of a fractal, as a preset pattern, can also be applied in laser induced refractive index change, in which a lens of the eye can also be irradiated besides the cornea to obtain a refractive index change. In particular, cavitation bubbles are not generated in this URIC method, but one achieves a refractive index change by molecular changes in the tissue.

Overall, the examples show how a regularly arranged diffraction structure can be interrupted by the invention in that virtually irregular structures are scanned by fractal scan patterns. In incisions, such curves can be scanned to generate the incision surfaces without the above mentioned side effects. In LIRIC applications too, such curves can be scanned to still achieve the desired characteristics of an extensive index change or a Fresnel lens.

What is claimed is:

1. A method for controlling an ophthalmological laser of a treatment apparatus for treatment of a human or animal eye, comprising:
    controlling the ophthalmological laser using a control device of the treatment apparatus such that the ophthalmological laser emits pulsed laser pulses in a shot sequence in a preset pattern into the eye,
    wherein the laser pulses individually interact with a tissue of the eye for treatment of the eye,
    wherein the ophthalmological laser is controlled such that the preset pattern of a space-filling curve is irradiated into the tissue of the eye, and
    wherein the space-filling curve describes a contiguous curve, which passes through the tissue of the eye to be treated.

2. The method according to claim 1, wherein the space-filling curve is shaped in a self-avoiding manner.

3. The method according to claim 1, wherein the space-filling curve is a fractal.

4. The method according to claim 3, wherein the fractal is one of a Gosper curve, a Hilbert curve or a Peano curve.

5. The method according to claim 1, wherein the ophthalmological laser is controlled such that the laser pulses generate the space-filling curve in a continuous manner.

6. The method according to claim 1, wherein the ophthalmological laser is controlled such that the laser pulses generate the space-filling curve either line by line or in a concentric or spiral manner.

7. The method according to claim 1, wherein the laser pulses are emitted into a cornea and/or a lens of the eye.

8. A control device, which is configured to perform a method according to claim 1.

9. A treatment apparatus with at least one ophthalmological laser for treatment of a human or animal eye using photodisruption and/or photoablation and/or a laser induced refractive index change, and at least one control device according to claim 8.

10. The treatment apparatus according to claim 9, wherein the at least one ophthalmological laser is formed to emit laser pulses in a wavelength range between 300 nm and 1400 nm, at a respective pulse duration between 1 fs and 1 ns, and a repetition frequency of greater than 10 kHz.

11. The treatment apparatus according to claim 10, wherein the at least one ophthalmological laser is formed to emit laser pulses in a wavelength between 700 nm and 1200 nm, at a respective pulse duration between 10 fs and 10 ps, and a repetition frequency between 100 kHz and 100 MHz.

12. The treatment apparatus according to claim 9, wherein the at least one ophthalmological laser is formed to emit laser pulses in a wavelength range between 150 nm and 250 nm, at a respective pulse duration between 1 fs and 100 ns, and a repetition frequency of greater than 100 Hz.

13. The treatment apparatus according to claim 12, wherein the at least one ophthalmological laser is formed to emit laser pulses in a wavelength between 175 nm and 215 nm, at a respective pulse duration between 10 ps and 10 ns, and a repetition frequency between 400 Hz and 10 kHz.

14. The treatment apparatus according to claim 9,
wherein the control device comprises at least one storage device for at least temporary storage of at least one control dataset, wherein the control dataset or datasets include(s) control data for positioning and/or focusing individual laser pulses in the eye; and
the treatment apparatus further includes at least one beam deflection device for beam guidance and/or beam shaping and/or beam deflection and/or beam focusing of a laser beam of the at least one ophthalmological laser.

15. A non-transitory computer-readable medium storing instructions that, when executed by a processor, cause a treatment apparatus, which includes at least one ophthalmological laser for treatment of a human or animal eye by means of photodisruption and/or photoablation and/or a laser induced refractive index change and at least one control device, to execute a method comprising:
controlling the at least one ophthalmological laser using the at least one control device of the treatment apparatus such that the at least one ophthalmological laser emits pulsed laser pulses in a shot sequence in a preset pattern into the eye,
wherein the laser pulses individually interact with a tissue of the eye for treatment of the eye,
wherein the at least one ophthalmological laser is controlled such that the preset pattern of a space-filling curve is irradiated into the tissue of the eye, and
wherein the space-filling curve describes a contiguous curve, which passes through the tissue of the eye to be treated.

* * * * *